United States Patent
Groskopf et al.

(10) Patent No.: US 10,207,053 B2
(45) Date of Patent: Feb. 19, 2019

(54) DRUG DELIVERY DEVICE FOR DRUG SUSPENSIONS

(75) Inventors: Roger W. Groskopf, Saddle Brook, NJ (US); Lionel Vedrine, Palo Alto, CA (US); Michael C. Ratigan, Mahwah, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 322 days.

(21) Appl. No.: 13/422,315

(22) Filed: Mar. 16, 2012
(Under 37 CFR 1.47)

(65) Prior Publication Data
US 2013/0245559 A1    Sep. 19, 2013

(51) Int. Cl.
*A61M 5/24* (2006.01)
*A61M 5/28* (2006.01)
*A61M 5/34* (2006.01)

(52) U.S. Cl.
CPC ........ *A61M 5/2448* (2013.01); *A61M 5/2466* (2013.01); *A61M 5/284* (2013.01); *A61M 5/343* (2013.01)

(58) Field of Classification Search
CPC ........ A61M 5/3294; A61M 2001/3494; A61M 5/165; A61M 5/3145; A61M 2005/31516; A61M 5/31; A61M 5/284; A61M 5/343; A61M 5/3129; A61M 5/3134; A61M 5/347
USPC .............. 604/82–92, 184, 200–206, 218
See application file for complete search history.

(56) References Cited

U.S. PATENT DOCUMENTS

| | | | | |
|---|---|---|---|---|
| 2,646,798 A | * | 7/1953 | Brown | A61M 5/24 604/201 |
| 2,688,967 A | | 9/1954 | Huber | |
| 2,798,487 A | * | 7/1957 | Ferguson | A61M 5/28 604/238 |
| 3,308,821 A | * | 3/1967 | Shields | A61M 5/286 222/81 |
| 3,820,542 A | * | 6/1974 | Hurschman | 604/196 |
| 4,553,962 A | * | 11/1985 | Brunet | 604/198 |

(Continued)

FOREIGN PATENT DOCUMENTS

| | | |
|---|---|---|
| EP | 0144551 A1 | 6/1985 |
| EP | 1266669 A1 | 12/2002 |

(Continued)

*Primary Examiner* — Bhisma Mehta
*Assistant Examiner* — Hamza Darb
(74) *Attorney, Agent, or Firm* — The Webb Law Firm

(57) ABSTRACT

In one aspect of the subject invention, a drug delivery device is provided which includes a reservoir for containing a medicament and has a proximal end and a distal end, the medicament including a suspension of solids in a liquid carrier. Further, the drug delivery device includes a needle in fluid communication with the reservoir and having a distal end for injection into a patient, and a proximal end in the reservoir. An accumulation surface is defined at least partially about the needle, distally of the proximal end of the needle. The accumulation surface defines a distally-extending indentation which is sized and shaped to collect, during use, solids that come out of suspension. Advantageously, with the subject invention, the accumulation surface allows for solids to accumulate at a location spaced from the proximal end of the needle, thereby minimizing the possibility of clogging the needle.

10 Claims, 5 Drawing Sheets

(56) References Cited

U.S. PATENT DOCUMENTS

| | | | |
|---|---|---|---|
| 4,599,082 A | | 7/1986 | Grimard |
| 5,017,191 A | | 5/1991 | Yamada et al. |
| 5,318,536 A | * | 6/1994 | Williams .............. A61M 5/322 604/110 |
| 5,489,266 A | | 2/1996 | Grimard |
| 5,554,125 A | * | 9/1996 | Reynolds ................ A61J 1/062 604/187 |
| 5,725,500 A | | 3/1998 | Micheler |
| 5,919,169 A | * | 7/1999 | Grams .................. A61M 5/344 604/240 |
| 5,997,511 A | * | 12/1999 | Curie et al. .................... 604/195 |
| 2004/0236273 A1 | | 11/2004 | Tanaka et al. |
| 2008/0234632 A1 | | 9/2008 | Hasegawa |
| 2010/0292656 A1 | * | 11/2010 | Groskopf ............ A61M 5/3134 604/200 |
| 2012/0209171 A1 | | 8/2012 | Vedrine et al. |

FOREIGN PATENT DOCUMENTS

| | | |
|---|---|---|
| GB | 430263 | 6/1935 |
| JP | 6148377 A | 3/1986 |
| JP | 7213608 A | 8/1995 |
| JP | 999034 A | 4/1997 |
| JP | 3325565 B2 | 7/2002 |
| JP | 200352823 A | 2/2003 |
| JP | 2005089837 A1 | 9/2005 |
| JP | 2007283132 A | 11/2007 |
| JP | 2010540122 A | 12/2010 |
| WO | 2005102423 A1 | 11/2005 |
| WO | 2009061480 A1 | 5/2009 |
| WO | 2009092084 A1 | 7/2009 |
| WO | 2012025550 A2 | 3/2012 |

* cited by examiner

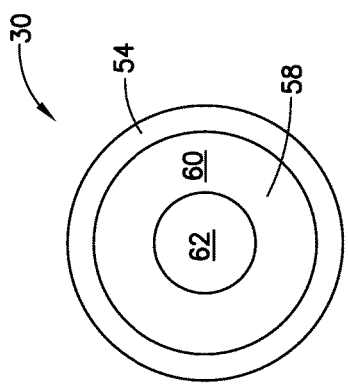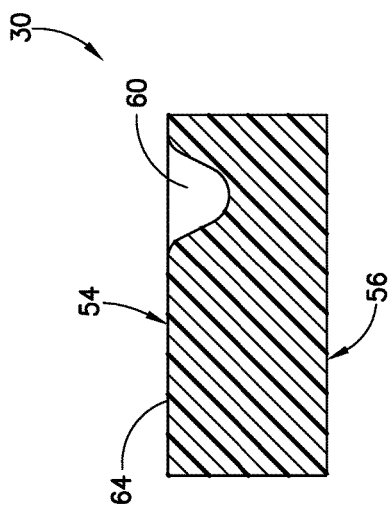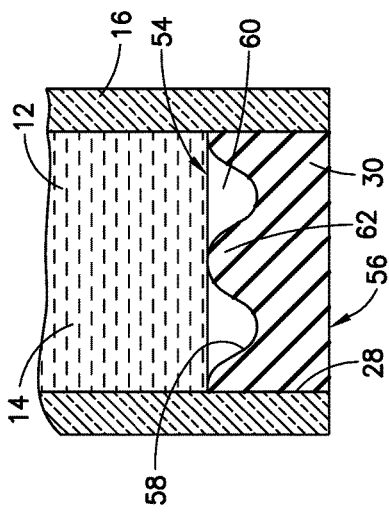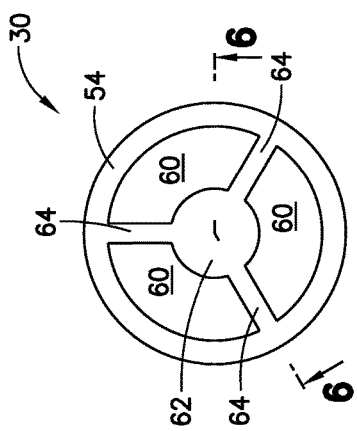

DRUG DELIVERY DEVICE FOR DRUG SUSPENSIONS

FIELD OF THE INVENTION

This invention relates to drug delivery devices for addressing the problems associated with solids coming out of drug suspension.

BACKGROUND OF THE INVENTION

Certain drugs or medicaments (those terms being used interchangeably herein) are preferably provided in powder or dry form (e.g., lyophilized form). Such powdered drugs are commonly suspended in a liquid diluent or carrier to allow delivery to an individual through injection. The powder drug is combined with the diluent prior to injection and administered in solution form. Drug delivery systems typically have a reservoir with a large diameter, for example a syringe barrel or drug cartridge, for containing the drug solution.

Prior art devices have been developed that provide a diluent and dry substance in separate chambers of a common container or reservoir, with the container being configured to permit the flow of the diluent to the dry substance to cause mixing thereof in forming a solution. For example, U.S. Pat. No. 4,874,381 to Vetter is directed to an injector configured for mixing, while U.S. Pat. No. 4,968,299 to Ahlstrand et al. is directed to a drug cartridge for mixing.

However, due to differences in density of solids and liquids in a solid/liquid suspension, the relative velocities of the two suspension constituents may be different, thus leading to possible separation of the solid particles out of solution. Further, certain drugs are capable of being mixed and then stored for a period of time. During the storage period, solids may have a tendency to separate out of the liquid carrier. Separation of the solids from the liquid is problematic for many reasons, for example, the separation may result in delivery of an insufficient or excessive dose of the drug to the individual. Further, when solids become separated from the liquid, gravitational forces may drive the solids towards the lower end of the reservoir (typically, the patient end), which is proximal to the opening of the needle cannula or other dispensing apertures. This collection of solids proximal to the needle opening or dispensing aperture is undesirable, as it may cause clogging of the needle opening.

SUMMARY OF THE INVENTION

In one aspect of the subject invention, a drug delivery device is provided which includes a reservoir for containing a medicament and has a proximal end and a distal end, the medicament including a suspension of solids in a liquid carrier. Further, the drug delivery device includes a needle in fluid communication with the reservoir and having a distal end for injection into a patient, and a proximal end in the reservoir. An accumulation surface is defined at least partially about the needle, distally of the proximal end of the needle. The accumulation surface defines a distally-extending indentation which is sized and shaped to collect, during use, solids that come out of suspension. Advantageously, with the subject invention, the accumulation surface allows for solids to accumulate at a location spaced from the proximal end of the needle, thereby minimizing the possibility of clogging the needle.

In a second aspect of the subject invention, a drug delivery device is provided herein which includes a barrel having a proximal end and a distal end. The barrel at least partially defines a reservoir for containing a medicament, the medicament including a suspension of solids in a liquid carrier. A needle is in fluid communication with the reservoir and has a distal end for injection into a patient, and a proximal end in the reservoir. A plunger is provided in the reservoir, the plunger being selectively movable for urging the suspension from the reservoir through the needle. Further, the drug delivery device includes at least one agitator disposed in the reservoir in communication with the suspension, the agitator configured to agitate the suspension during movement of the plunger. Advantageously, with the subject invention, an agitator may be provided which agitates the suspension to cause mixing thereof thereby minimizing the amount of solids out of solution in the suspension.

As will be recognized by those skilled in the art, the various aspects of the subject invention described herein may be used singularly or in any combination.

These and other features of the invention will be better understood through a study of the following detailed description and accompanying drawings.

BRIEF DESCRIPTION OF THE DRAWINGS

FIG. 3 is an enlarged view of a septum usable with the subject invention;

FIG. 4 is a top plan view of the septum of FIG. 3;

FIG. 5 is a top plan view of a variation of a septum usable with the subject invention;

FIG. 6 is a cross-sectional view taken along line 6-6 of FIG. 5;

DETAILED DESCRIPTION OF THE INVENTION

Figure 1:
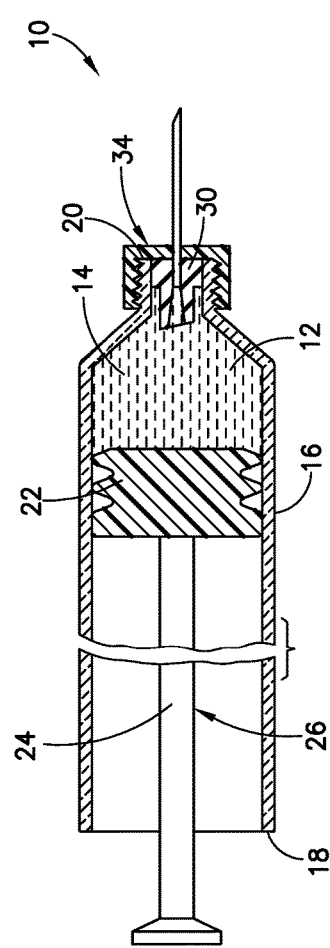
FIG. 1 is a schematic of the drug delivery device of the subject invention shown as a syringe.
Figure 2:
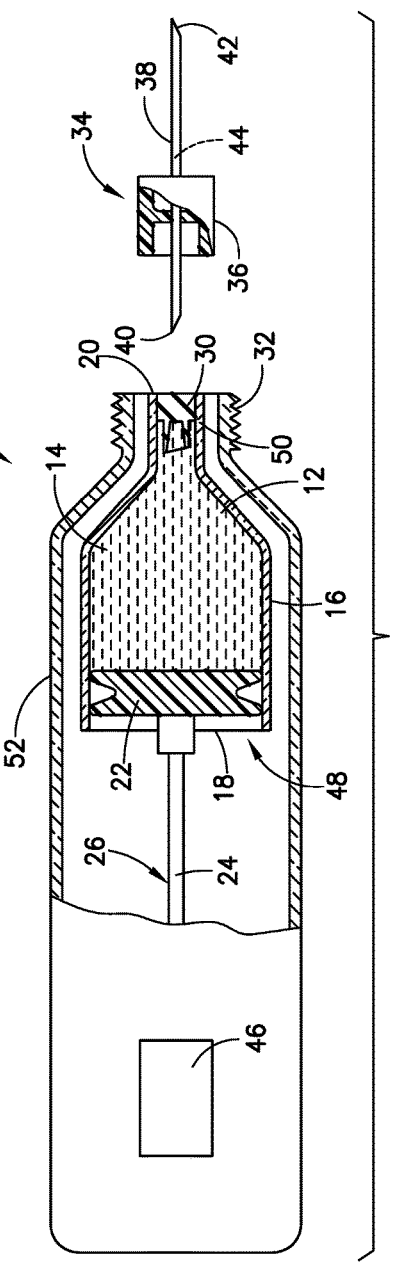
FIG. 2 is a schematic of the drug delivery device of the subject invention shown as a pen injector with a drug cartridge.

With reference to the figures, a drug delivery device 10 is shown for delivery of a drug in a fluid suspension to an individual. As will be appreciated by those skilled in the art, the drug delivery device 10 may be of various forms. With reference to FIGS. 1 and 2, the drug delivery device 10 may be in the form of a syringe (FIG. 1) or a pen injector or the like (FIG. 2). In any regard, the drug delivery device 10 includes a reservoir 12 in which a suspension 14 is maintained.

With reference to FIG. 1, the drug delivery device 10 includes a barrel 16. The barrel 16 includes a proximal end 18 and a distal end 20. As used herein, the term "proximal" shall refer to the end of the component further away from the injection site (i.e., the "non-patient end"), while the term "distal" shall refer to the end toward the injection site (i.e., the "patient end"). As known in the art, one or more stoppers 22 may be disposed in the barrel 16 in liquid-tight engagement therewith. A plunger rod 24 extends from the stopper 22 in a proximal direction, e.g., so as to be accessible at the proximal end 18 of the barrel 16. The stopper 22 and the plunger rod 24 together form a plunger 26 which is usable for urging the suspension 14 from the reservoir 12 as described below.

As best shown in FIG. 3, an opening 28 is defined in the distal end 20 of the barrel 16 which permits access to the reservoir 12. The opening 28 is sealed by a septum 30, which is preferably made of an elastomeric material, as is well known in the art. The barrel 16 may be formed with a reduced diameter adjacent to the distal end 20 so as to define a neck 32 onto which a pen needle assembly 34 may be mounted. The pen needle assembly 34 includes a hub 36 to which is mounted a needle cannula 38. The hub 36 is formed to mount onto the barrel 16, such as at the neck 32, through the use of cooperating mounting members, such as threads, or may be affixed thereto (such as by adhesive or fusion). Alternatively, the hub 36 may be formed integrally with the barrel 16. The needle cannula 38 includes a proximal end 40, formed to extend into the reservoir 12 with the hub 36 being mounted to the barrel 16, and a distal end 42, formed for insertion into a patient. The needle cannula 38 extends through the septum 30 to access the reservoir 12. With mounting the pen needle assembly 34 onto the barrel 16, the needle cannula 38 pierces through the septum 30. A lumen 44 extends the length of the needle cannula 38 to communicate the proximal end 40 with the distal end 42.

As shown in FIG. 1, the reservoir 12 may be defined by a combination of various components, including the barrel 16, the stopper 22, and the septum 30. As is well known in the art, with the pen needle assembly 34 being mounted to the barrel 16, particularly with the proximal end 40 of the needle cannula 38 extending into the reservoir 12, distal advancement of the plunger 26 will cause the suspension 14 to be urged through the needle cannula 38.

With reference to FIG. 2, the drug delivery device 10 is shown in the form of a pen injector. The elements as discussed above with reference to FIG. 1 are similarly numbered. In the form of a pen injector, a dose-setting mechanism, schematically shown as a box 46, may be provided. Dose-setting mechanisms for pen injectors are well known in the prior art. In addition, in FIG. 1, the plunger 26 is shown to be of the manually driven type. In both variations of FIGS. 1 and 2, and in other possible configurations of the drug delivery device 10, the plunger 26 may be configured to be manually, semi-automatically, or automatically driven.

With a pen injector configuration, a drug cartridge 48 is typically provided. The drug cartridge 48 may include the barrel 16, the stopper 22 and the septum 30 and define the reservoir 12. The main difference between the drug cartridge 48 and the configuration of FIG. 1 is that the pen needle assembly 34 is mounted to neck 50 defined on outer barrel 52 of the drug delivery device 10, rather than being mounted to the barrel 16.

The suspension 14 includes a medicament for delivery into an individual. The suspension 14 includes solid components held in a liquid carrier. The active medicament agent or agents may be in the solid components of the suspension 14 and/or in the liquid carrier. The suspension 14 may contain solids dissolved to varying degrees, including at least some solids completely dissolved, or it may include solid particles, suspended in the liquid carrier. The suspension 14 may be pre-mixed before it is disposed in the reservoir 12, or it may be mixed after it has been disposed in the reservoir 12. For example, the reservoir 12 may house a liquid diluent and a solid drug in separate compartments, such as in a reconstitution arrangement as is known in the art, where the two components are mixed prior to delivery to an individual. Examples of suitable reconstitution arrangements may be found, for example, in U.S. Pat. No. 4,874,381 and in U.S. Pat. No. 4,968,299, the contents of which are incorporated by reference herein.

During storage or use of the drug delivery device 10, the solid components of the suspension 14 may come out of solution. With reference to FIG. 3, the septum 30 is shown within the barrel 16. The septum 30 includes a proximally-facing surface 54 and a distally-facing surface 56. It is preferred that on the proximally-facing surface 54 an accumulation surface 58 be defined at least partially about the needle cannula 38. As shown in FIG. 1, the accumulation surface 58 is located distally of the proximal end 40 of the needle cannula 38 with the proximal end 40 being in the reservoir 12. The accumulation surface 58 defines at least one distally-extending indentation 60 which is sized and shaped to collect, during use, solids that may come out of the suspension 14. With reference to FIG. 4, in a preferred embodiment, the indentation 60 is continuous and circumscribes the needle cannula 38. In addition, in cross-section, the indentation 60 is trough shaped. With the accumulation surface 58, solid particles that come out of the suspension 14, particularly those which fall towards the distal end 20 of the barrel 16 under gravitational effects, may collect in the indentation 60. The indentation 60 acts as a well in which the solid particles may be at least partially submersed, thus minimizing exposure to the suspension 14. The lessened exposure minimizes the ability of the solid particles to re-float into the suspension 14 proximate to the proximal end 40 of the needle cannula 38.

Preferably, the proximally-facing surface 54 also includes a proximally-extending protrusion 62 located adjacent to the accumulation surface 58. The protrusion 62 is preferably sized and positioned so that the needle cannula 38 extends therethrough during use.

As will be appreciated by those skilled in the art, the indentation 60 may be formed with various configurations, including being formed as one or more discontinuous indentations. For example, the indentation 60 may be formed as one or more dimples in the proximally-facing surface 54.

With reference to FIGS. 5 and 6, one or more ribs 64 may be defined on the accumulation surface 58 so as to radiate outwardly from the needle cannula 38 and disposed to extend at least partially across the indentation 60. As shown particularly in FIG. 6, the ribs 64 may define dividers in the indentation 60 which segregate the indentation 60 into one or more compartments. This compartmentalization further isolates any solid particles which may be contained in the indentation 60 from the suspension 14.

Figure 7:
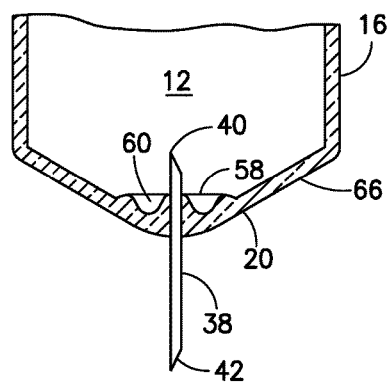
FIG. 7 is a schematic showing a variation of the subject invention with a staked needle configuration.
Figure 9:
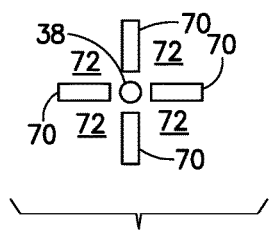
FIGS. 9 and 10 are schematics showing a second embodiment of an agitator usable with the subject invention.
Figure 10:
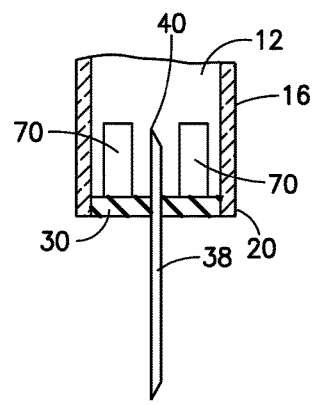
Figure 11:
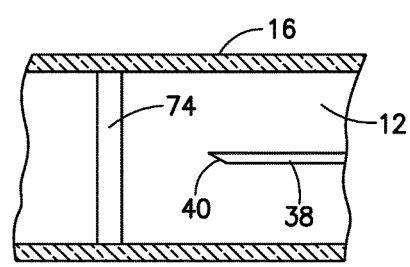
FIGS. 11 and 12 are schematics showing a third embodiment of an agitator usable with the subject invention.
Figure 12:
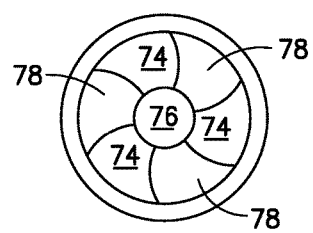

With reference to FIG. 7, the needle cannula 38 may be directly fixed to the barrel 16, such as in a staked needle configuration. Here, the accumulation surface 58 may be defined directly on the barrel 16, particularly at the distal end 20 of the barrel 16. The distal end 20 of the barrel 16 may have a proximally-facing portion 66 located about the needle cannula 38. Preferably, the accumulation surface 58 is defined on the proximally-facing portion 66. The proximally-facing portion 66 may be tapered and/or arcuately formed. The accumulation surface 58 may be defined as described above.

Figure 8A:
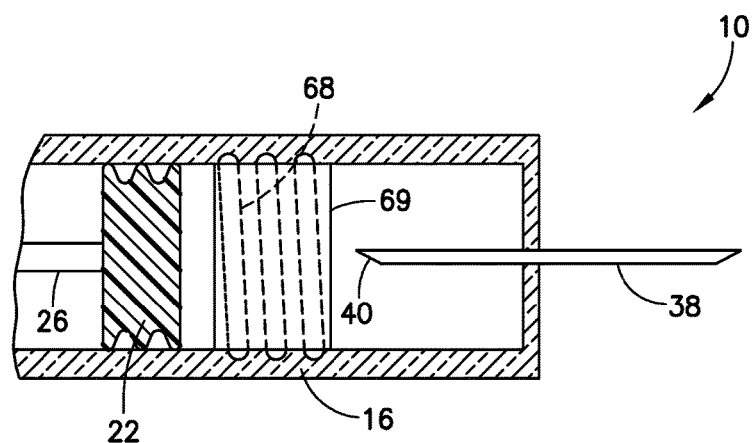
FIGS. 8A-8D are schematics showing an agitator usable with the subject invention.
Figure 8B:
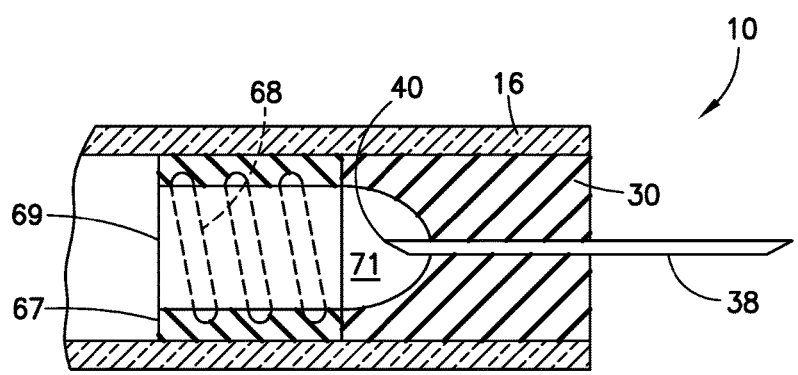
Figure 8C:
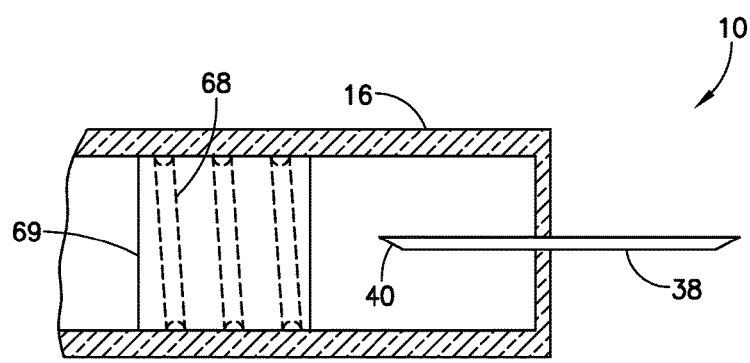
Figure 8D:
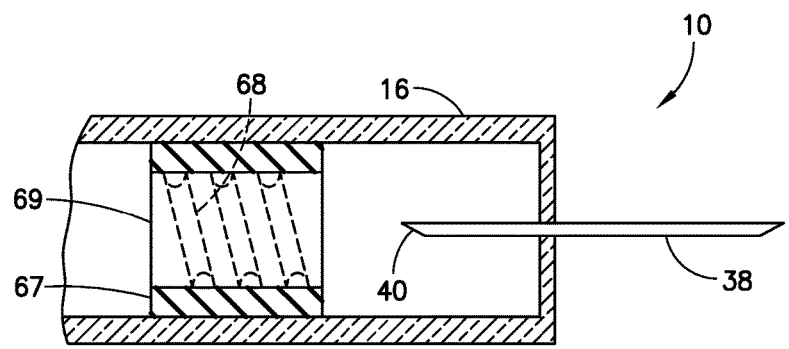

In addition to providing a manner by which solid particles may be accumulated, it may be desired to provide features for agitating the suspension 14, thereby possibly causing sufficient mixing and causing solid particles to go back into solution in the suspension 14. An agitator may be provided in the reservoir 12 configured to cause agitation upon movement of the plunger 26, particularly distal movement of the plunger 26. Thus, as the suspension 14 is driven towards the needle cannula 38 under force of movement of the plunger 26, the suspension 14 is caused to flow in a generally distal direction. In one embodiment, with reference to FIGS. 8A-8D, the agitator may be one or more channels 68 formed in communication with the suspension 14. Preferably, a single helical channel 68 of several windings is provided. The channels 68 may be formed in the barrel 16 (FIG. 8A) and/or an annular component 67 disposed inside the barrel 16 (FIG. 8B). The component 67 may be formed of elastomeric material. A stationary plug 69 may be disposed inside the barrel 16 (FIG. 8A), and inside the component 67 (FIG. 8B) if used, configured so as to seal portions of the channels 68 in defining a continuous flowpath therethrough. The flowpath is closed so that the suspension 14 may travel about the stationary plug 69. In addition, or alternatively, one or more of the channels 68 may be formed in the plug 69, as shown in FIGS. 8C and 8D.

The plunger 26 will force the suspension 14 through the channels 68 about the plug 69. Distal movement of the plunger 26 will impart distally directed momentum to the suspension 14 such that the suspension 14 will generally move distally down the channels 68. The channels 68 will provide a rotational aspect to the flow, thus causing turbulence in minimizing separation in the suspension 14. It is preferred that the channels 68 be located at least partially proximally of the proximal end 40 of the needle cannula 38. In this manner, any mixing of the suspension 14 may be done proximally of the needle cannula 38 thereby increasing the possibility of mixing the suspension 14 and then causing the mixed suspension to be delivered through the needle cannula 38. Other configurations of the channels 68 are possible. In addition, the channels 68 may be wholly or partially located distally of the proximal end 40 of the needle cannula 38.

The plug 69 preferably fits sufficiently tightly against the barrel 16 and/or the annular component 67 to be generally stationary. In addition, as shown in FIG. 8B, the annular component 67 may be located adjacent to, fixed to, or formed unitarily with, the septum 30 with a pocket 71 being optionally defined in the septum 30 to accommodate the proximal end 40 of the needle cannula 38.

With reference to FIGS. 9 and 10, a second embodiment of an agitator is depicted. In particular, one or more fins 70 may be disposed about the needle cannula 38, particularly proximally of the proximal end 40 of the needle cannula 38. As shown in FIG. 10, the fins 70 may be formed to extend from the septum 30. In addition, or alternatively, the fins 70 may be formed on the barrel 16 and/or formed on an annular plug disposed immovably in the barrel 16.

One or more of the fins 70 may be provided. Preferably, the fins 70 are plate shaped and extend in a distal direction from the septum 30 or the distal end 20 of the barrel 16. Various shapes and configurations of the fins 70 are possible. Channels 72 are formed between the fins 70 into which the suspension 14 is urged under force of movement of the plunger 26. The fins 70 reduce flow area and thus cause the suspension 14 to accelerate through the channels 72 in passing to the proximal end 40 of the needle cannula 38. This increase in velocity helps maintain the suspension thereby minimizing separation therein. In addition, the fins 70 direct any of the suspension 40 which by-passes the proximal end 40 of the needle cannula 38 in a generally distal direction. The fluid is directed to strike against, and rebound from, the septum 30 and/or the distal end 20 of the barrel 16. Upon rebounding, the suspension 14 is forced to mix with the suspension 14 that is flowing from behind.

In a further embodiment of an agitator, and with reference to FIGS. 11 and 12, at least one stationary vane 74 is disposed in the reservoir 12. The vanes 74 may extend to a central hub 76. The vanes 74 are spaced apart to define voids 78 therebetween. With distal movement of the suspension 14, under force of movement of the plunger 26, the suspension 14 is urged through the voids 78. The vanes 74 are configured, such as being bent, twisted and/or rounded, such that movement of the suspension 14 through the voids 78 results in acceleration of the suspension 14. Again, the increase in velocity assists in minimizing separation in the suspension 14. In addition, the suspension 14 experiences turbulence and, thus, mixing, which results in minimization of separation in the suspension 14. As shown in FIG. 11, it is preferred that the vanes 74 be located proximally of the proximal end 40 of the needle cannula 38. As will be appreciated by those skilled in the art, one or more of the vanes 74 may be utilized.

What is claimed is:

1. A drug delivery device comprising:

a unitary reservoir for containing a medicament and having a proximal end and a distal end, the distal end having a proximal-facing surface formed thereon, the medicament comprising a suspension of solids in a liquid carrier; and a needle directly affixed to the distal end of the unitary reservoir and the proximal-facing surface and passing therethrough, said needle having a distal end for injection into a patient and a proximal end in said reservoir, said needle, in constant fluid communication with said reservoir, wherein the proximal-facing surface is defined at least partially about said needle, distally of said proximal end of said needle, said proximal-facing surface comprising an accumulation surface defined by a distally-extending trough-shaped indentation sized and shaped to collect, during use, solids that come out of suspension, said indentation being spaced from and circumscribing said needle, said proximal-facing surface also defining a proximally-extending protrusion located adjacent to said accumulation surface, said needle passing through said protrusion, wherein said protrusion comprises at least one rib located on said proximally-facing surface and radiating outwardly from said protrusion to extend at least partially across said indentation.

2. The device as in claim 1, wherein the at least one rib extends from the protrusion across an entire width of said indentation.

3. The device as in claim 1, wherein said accumulation surface comprises a plurality of separate compartments, said compartments separated by said at least one rib.

4. The device as in claim 1, wherein said accumulation surface comprises a tapered portion or an arcuate portion extending between a trough of said indentation and a crest of said protrusion.

5. The device of claim 1, wherein the proximal-facing surface comprises a tapered portion extending between a trough of said indentation and a crest of said protrusion.

6. The device of claim 1, wherein the proximal-facing surface comprises an arcuate portion extending between a trough of said indentation and a crest of said protrusion.

7. A drug delivery device comprising:
a unitary barrel at least partially defining a reservoir for containing a medicament and having a longitudinal wall extending between a proximal end and a distal end, said distal end of said barrel including a proximal-facing portion, the medicament comprising a suspension of solids in a liquid carrier;
a needle directly affixed to the distal end of the unitary barrel and the proximal-facing portion and passing therethrough, said needle having a distal end for injection into a patient and a proximal end in said reservoir, said needle in constant fluid communication with said reservoir,
wherein said proximal-facing portion is defined at least partially about said needle, distally of said proximal end of said needle,
wherein the proximal-facing portion of the barrel includes an accumulation surface formed directly thereon comprising at least one indentation sized and shaped to collect, during use, solids that come out of the suspension, and wherein a trough of said at least one indentation is spaced from said longitudinal wall of said barrel.

8. The device as in claim 7, wherein said accumulation surface comprises a tapered portion or an arcuate portion extending between said trough of said at least one indentation and said longitudinal wall.

9. The device of claim 7, wherein the proximal-facing portion comprises a tapered portion extending between said trough of said at least one indentation and said longitudinal wall.

10. The device of claim 7, wherein the proximal-facing portion comprises an arcuate portion extending between said trough of said at least one indentation and said longitudinal wall.

* * * * *